US012601729B2

(12) United States Patent
Wang et al.

(10) Patent No.: US 12,601,729 B2
(45) Date of Patent: Apr. 14, 2026

(54) SYSTEM AND METHOD FOR REMOTELY MEASURING IMPEDANCE OF ROCK AND ORE SAMPLES

(71) Applicant: GIANT SEQUOIA AI TECHNOLOGY (CHANGSHA) LIMITED, Changsha (CN)

(72) Inventors: Xiaojie Wang, Changsha (CN); Rujun Chen, Changsha (CN); Xingsheng Chen, Changsha (CN); Shaoheng Chun, Changsha (CN); Shengjie Li, Changsha (CN); Zihui Wang, Changsha (CN); Hongchun Yao, Changsha (CN); Ruijie Shen, Changsha (CN); Zhitong Liu, Changsha (CN); Shenglan Hou, Changsha (CN); Feifei Wang, Changsha (CN)

(73) Assignee: GIANT SEQUOIA AI TECHNOLOGY(CHANGSHA) LIMITED, Changsha (CN)

( * ) Notice: Subject to any disclaimer, the term of this patent is extended or adjusted under 35 U.S.C. 154(b) by 274 days.

(21) Appl. No.: 18/577,233

(22) PCT Filed: Dec. 27, 2022

(86) PCT No.: PCT/CN2022/142137
§ 371 (c)(1),
(2) Date: Jan. 5, 2024

(87) PCT Pub. No.: WO2023/125465
PCT Pub. Date: Jul. 6, 2023

(65) Prior Publication Data
US 2024/0219365 A1     Jul. 4, 2024

(30) Foreign Application Priority Data
Dec. 30, 2021     (CN) ......................... 202111658524.6

(51) Int. Cl.
*G01N 33/24*     (2006.01)
*G08C 17/02*     (2006.01)

(52) U.S. Cl.
CPC ............. *G01N 33/24* (2013.01); *G08C 17/02* (2013.01)

(58) Field of Classification Search
CPC ......... G01N 33/24; G08C 17/02; G01R 27/02
See application file for complete search history.

*Primary Examiner* — Tarun Sinha
(74) *Attorney, Agent, or Firm* — ARC IP Law, PC; Joseph J. Mayo

(57) ABSTRACT

The present disclosure provides a system and method for remotely measuring impedance of rock and ore samples, and relates to the field of measurement of impedance of rock and ore samples. The method includes: establishing, by a wireless communication module, wireless network connection between a smart mobile device and a sample impedance tester; performing, by a parameter setting module in the smart mobile device, parameter acquisition setting and sample photographing, and storing acquired parameters and photos photographed for the samples; and sending, by the smart mobile device, a self-check command to the sample impedance tester to obtain self-check information of the sample impedance tester, and sending, by the smart mobile device, measurement configuration information and an acquisition command to an embedded control system.

18 Claims, 5 Drawing Sheets

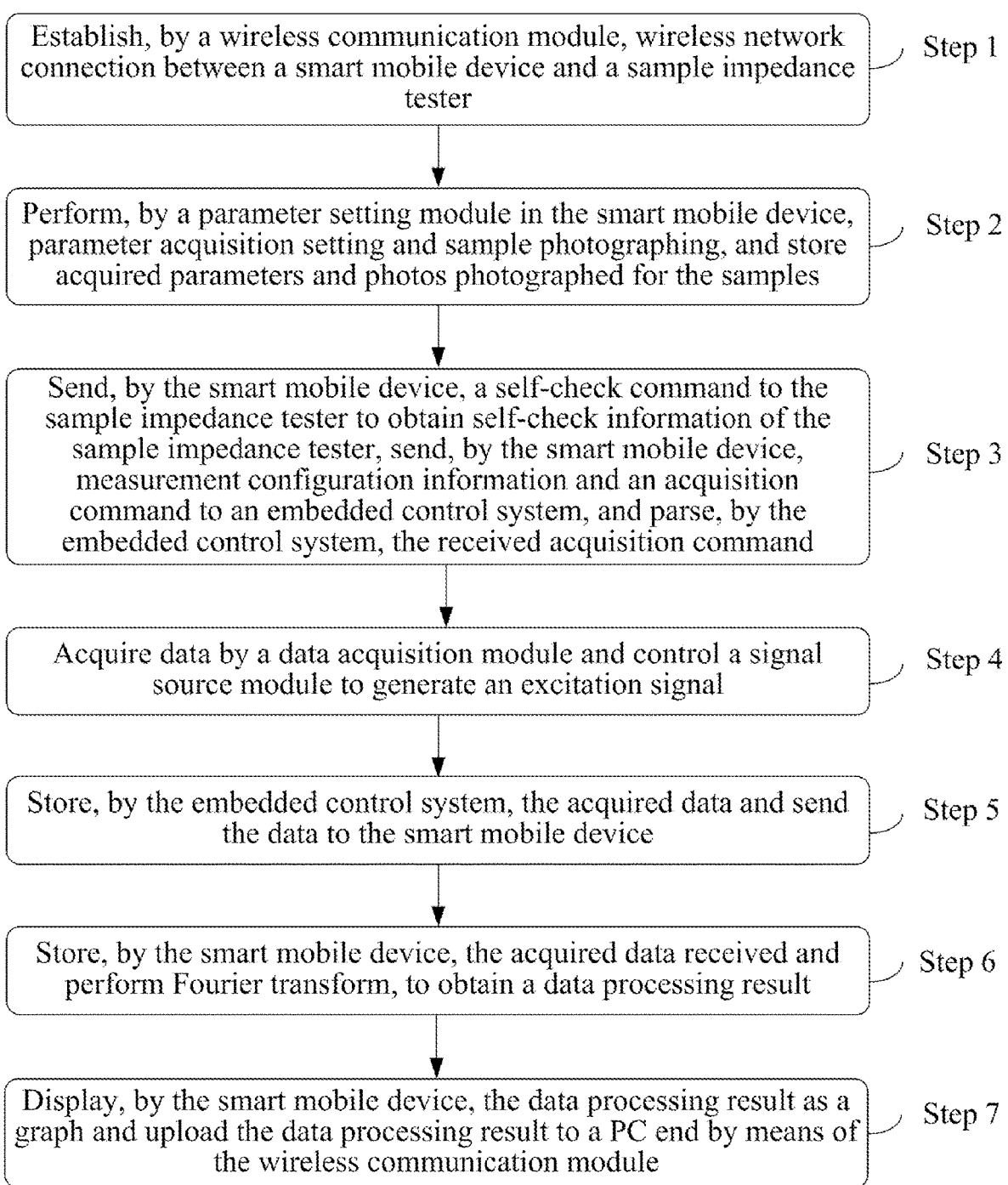

| Establish, by a wireless communication module, wireless network connection between a smart mobile device and a sample impedance tester | Step 1 |

| Perform, by a parameter setting module in the smart mobile device, parameter acquisition setting and sample photographing, and store acquired parameters and photos photographed for the samples | Step 2 |

| Send, by the smart mobile device, a self-check command to the sample impedance tester to obtain self-check information of the sample impedance tester, send, by the smart mobile device, measurement configuration information and an acquisition command to an embedded control system, and parse, by the embedded control system, the received acquisition command | Step 3 |

| Acquire data by a data acquisition module and control a signal source module to generate an excitation signal | Step 4 |

| Store, by the embedded control system, the acquired data and send the data to the smart mobile device | Step 5 |

| Store, by the smart mobile device, the acquired data received and perform Fourier transform, to obtain a data processing result | Step 6 |

| Display, by the smart mobile device, the data processing result as a graph and upload the data processing result to a PC end by means of the wireless communication module | Step 7 |

FIG. 1

SYSTEM AND METHOD FOR REMOTELY MEASURING IMPEDANCE OF ROCK AND ORE SAMPLES

CROSS REFERENCE TO RELATED APPLICATION

The present application is a national stage application of International Patent Application No. PCT/CN2022/142137, filed on Dec. 27, 2022, which claims priority to Chinese Patent Application No. 202111658524.6, filed with the China National Intellectual Property Administration on Dec. 30, 2021, and entitled "SYSTEM AND METHOD FOR REMOTELY MEASURING IMPEDANCE OF ROCK AND ORE SAMPLES", which is incorporated herein by reference in its entirety.

TECHNICAL FIELD

The present disclosure relates to the technical field of measurement of impedance of rock and ore samples, and in particular, to a system and method for remotely measuring impedance of rock and ore samples.

BACKGROUND

After the development of a variable frequency method, a phase induced polarization method, and the like, a complex resistivity method has become a spectrum induced polarization method mainly for measuring an amplitude and a phase spectrum. In the spectrum induced polarization method, a conventional resistivity method electrode apparatus is usually used to send an alternating current to the underground, then an apparent complex resistivity spectrum in an ultra-low frequency band ($f=10^{-2}–n\times10^2$ Hz) is observed, and physical characteristics of geoelectric anomalies are determined by studying amplitude spectrum and phase spectrum characteristics and spatial distribution reflected by a real part and an imaginary part of the observed apparent complex resistivity.

Currently, there are two types of indoor rock and ore sample impedance measuring instruments corresponding to the spectrum induced polarization method: one type is impedance-based analyzers or inductance-capacitance-resistance bridges, and the other is self-made measuring systems. A control system in the apparatus as an important part of the rock and ore impedance measuring instrument provides a function of controlling an acquisition system for data acquisition, data storage, data transmission, data preview and data processing, and is related to quality of subsequent data processing. However, the existing measuring instruments generally use an external signal source as an excitation source, and the control system with a personal computer (PC) and Windows software as the core often uses a bus and Ethernet for acquisition control and data transmission, so that it is impossible to uniformly configure the signal source and acquisition. The PC is relatively heavy in field survey, is not easy to carry, and has poor endurance. In addition, the use of the external signal source may make the measurement operation not intelligent enough, and remote measurement cannot be implemented by wired control. There are also control systems based on a personal digital assistant and Bluetooth communication in the market, but the transmission speed of Bluetooth is slow and the cost of the personal digital assistant is usually high. Most of software on the PC end is only used to receive data, lacking functions of data processing and display as a graph. Currently, with the rapid development of information technology, the above measuring apparatuses cannot meet requirements of the development of intelligent geophysical instruments and operations requiring portability.

SUMMARY

The present disclosure provides a system and method for remotely measuring impedance of rock and ore samples, aiming to solve the problems that a conventional measuring apparatus cannot implement remote measurement, and has low intelligence, poor endurance and slow data transmission speed.

To achieve the above purpose, the present disclosure provides a system for remotely measuring impedance of rock and ore samples, including:

a smart mobile device, where the smart mobile device includes a parameter setting module, an acquisition control module, a measurement result module, a data visualization module, a data upload module and a software navigation module, where the parameter setting module is configured to set various parameters of sample measurement, the acquisition control module is configured to control an acquisition control process of sample measurement, the measurement result module is configured to perform Fourier transform and calculation on received data and store the data to files of the smart mobile device, the data visualization module is configured to display a measurement result and original data on an interface as a graph, the data upload module is configured to upload various sample-related files in the smart mobile device to a personal computer (PC) end, and the software navigation module is configured to switch between various interfaces and perform function navigation;

a wireless communication module, where a first end of the wireless communication module is electrically connected to the smart mobile device, the wireless communication module includes a Bluetooth unit and a wireless fidelity (Wi-Fi) hotspot unit, the Bluetooth unit is configured to send a command, and the Wi-Fi hotspot unit is configured to transmit data; and a sample impedance tester, where the sample impedance tester is electrically connected to a second end of the wireless communication module, the sample impedance tester includes an embedded control system, a data acquisition module and a signal source module, where the embedded control system is configured to receive and send commands and data; a first end of the data acquisition module is electrically connected to the embedded control system, the data acquisition module is configured to receive a control command and acquire data, and a complex programmable logic device (CPLD)-based acquisition system is adopted for the data acquisition module; the signal source module is electrically connected to a second end of the data acquisition module, the data acquisition module is configured to receive a control command and generate an excitation signal, and a signal source board is adopted for the signal source module.

In the above system, the embedded control system includes:

a command parsing module, where the command parsing module includes a main control chip, a first end of the main control chip is electrically connected to the first end of the data acquisition module, and the command parsing module is configured to parse a string command from the smart mobile device into a 64-bit hardware command;

a data receiving and storage module, where the data receiving and storage module includes a secure digital (SD) card, the SD card is electrically connected to a second end of the main control chip, and the data receiving and storage module is configured to receive and store the data acquired by the data acquisition module; and a data sending module, where the data sending module includes a Bluetooth module and a Wi-Fi module, where a first end of the Bluetooth module is electrically connected to a third end of the main control chip, a second end of the Bluetooth module is electrically connected to a first end of the Bluetooth unit, and a second end of the Bluetooth unit is electrically connected to an Android phone and a first end of the Wi-Fi hotspot unit; a first end of the Wi-Fi module is electrically connected to a fourth end of the main control chip, a second end of the Wi-Fi module is electrically connected to a second end of the Wi-Fi hotspot unit, a third end of the Wi-Fi hotspot unit is electrically connected to the PC end, and the data sending module is configured to transmit data to the smart mobile device.

The present disclosure further provides a method for remotely measuring impedance of rock and ore samples, which is applied to the above system for remotely measuring impedance of rock and ore samples, including:

step 1: establishing, by a wireless communication module, wireless network connection between a smart mobile device and a sample impedance tester;

step 2: performing, by a parameter setting module in the smart mobile device, parameter acquisition setting and sample photographing, and storing acquired parameters and photos photographed for the samples;

step 3: sending, by the smart mobile device, a self-check command to the sample impedance tester to obtain self-check information of the sample impedance tester, sending, by the smart mobile device, measurement configuration information and an acquisition command to an embedded control system, and parsing, by the embedded control system, the received acquisition command;

step 4: acquiring data by a data acquisition module and controlling a signal source module to generate an excitation signal;

step 5: storing, by the embedded control system, the acquired data and sending the data to the smart mobile device;

step 6: storing, by the smart mobile device, the acquired data received and performing Fourier transform, to obtain a data processing result; and step 7: displaying, by the smart mobile device, the data processing result as a graph and uploading the data processing result to a PC end by means of the wireless communication module.

In the above method, step 1 specifically includes:

establishing, by the smart mobile device, wireless connection and communication with the embedded control system in the sample impedance tester by means of a Bluetooth unit and a Wi-Fi hotspot unit of the wireless communication module.

In the above method, step 2 specifically includes:

setting, by the parameter setting module in the smart mobile device, sample parameters, measurement control parameters, sample information and work area information, photographing the samples, storing, by a measurement result module, parameter setting information in an SQLite database, sending, by the parameter setting module, set parameter information to an acquisition control module, and receiving, by the acquisition control module, the parameters from the parameter setting module and controlling a number of measurement times and errors during measurement by means of the received parameters.

In the above method, step 3 specifically includes:

sending, by the smart mobile device, the self-check command to the sample impedance tester, receiving, by the sample impedance tester, the self-check command sent by the smart mobile device to obtain self-check information, sending, by the smart mobile device, measurement configuration information and an acquisition command to the embedded control system, the acquisition command including a signal frequency, a sampling frequency, a measurement signal pattern, a measurement signal amplitude value and a frequency tuning word, parsing, by the embedded control system, the acquisition command by means of a command parsing module, and parsing a plain code string into a 64-bit hardware protocol command and sending the command to the data acquisition module for acquisition control.

In the above method, step 4 specifically includes:

receiving, by the data acquisition module, a control command from the embedded control system to configure an analog-to-digital converter (ADC) and the signal source module, acquiring the data by the data acquisition module and transmitting the acquired data to the embedded control system, and receiving, by the signal source module, the control command from the data acquisition module and generating the excitation signal.

In the above method, step 5 specifically includes:

receiving, by a data receiving and storage module, the acquired data from the data acquisition module, storing, by the data receiving and storage module, the acquired data to an SD card of the embedded control system, and transmitting, by the data sending module, the acquired data to the smart mobile device.

In the above method, step 6 specifically includes:

storing, by the smart mobile device, the acquired data received, receiving, by the smart mobile device, a target data volume according to a data volume corresponding to a signal frequency designed by means of a frequency sweep algorithm, and then stopping receiving the acquired data and sending a command for stopping acquiring the data; performing, by the measurement result module, Fourier transform on the acquired data received from the data acquisition module, calculating the acquired data, obtaining a response generated by the rock and ore samples under excitation of the signal frequency, and storing original data and a measurement result, where the original data is time domain binary data and is directly stored in a file, and the measurement result is written into a text file in a fixed format.

In the above method, step 7 specifically includes:

reading, by a data visualization module, all previous measurement results and displaying all the previous measurement results on an interface as a graph by using an Android drawing framework, processing, by a data upload module, a sample photo, a time series file and a result file corresponding to each measured sample in a work area and a database file corresponding to the work area, building a local area network by using the smart mobile device, and uploading the entire work area file to the PC end by means of transmission control protocol (TCP) transmission.

The present disclosure has the following beneficial effects.

In the system and method for remotely measuring impedance of rock and ore samples according to the above embodiments of the present disclosure, 1. A smart mobile device is used to interact directly with a user, the operation is simple, and the smart mobile device is portable and intelligent; 2. STM32 based on a CortexM4 kernel is used as the core of an embedded control system to translate commands and store and transmit data, which features timely command response, fast interruption and low power consumption; 3. A portable signal source further reduces the volume of an instrument, and facilitates spectrum induced polarization measurement of rocks and ores by a user; 4. Bluetooth connection is used for wireless control, an operator can operate the instrument more flexibly, thereby avoiding the influence of factors such as unfavorable topography and vegetation; 5. Wireless fidelity (Wi-Fi) connection is used to transmit data, thereby achieving a higher data transmission speed; 6. A sample impedance tester is completely sealed, which improves dustproof, shockproof and moistureproof capabilities of the sample impedance tester; 7. Acquired data is timely transmitted to the smart mobile device, and the smart mobile device can timely process and calculate data, display results as graphs and dynamically display calculation parameters, which facilitates mastering and monitoring of the measurement process by the user, thereby reducing a rework rate during the measurement and improving measurement efficiency; and 8. Application software based on the smart mobile device has rich and flexible programming and development capabilities, leaving a large design margin for the application of novel methods and novel functions in the future, which facilitates expansion, maintenance and upgrading.

BRIEF DESCRIPTION OF THE DRAWINGS

To describe the technical solutions in embodiments of the present disclosure or in the prior art more clearly, the accompanying drawings required in the embodiments are briefly described below. Apparently, the accompanying drawings in the following description show merely some embodiments of the present disclosure, and other accompanying drawings can be derived from these accompanying drawings by those of ordinary skill in the art without creative efforts.

FIG. 1 is a flowchart of the present disclosure;

DESCRIPTION OF REFERENCE NUMERALS

Figure 2:
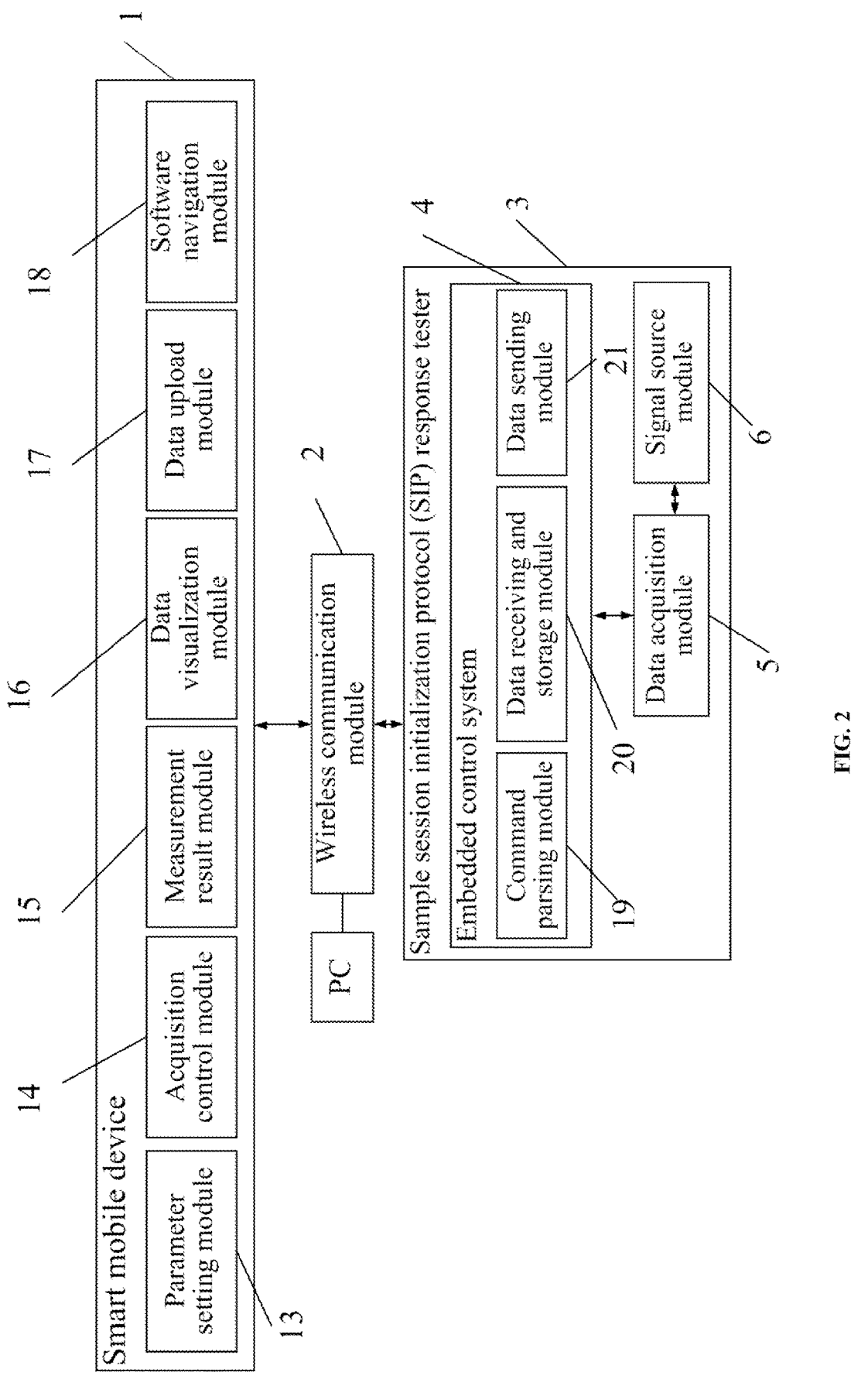
FIG. 2 is a schematic diagram of an overall structure according to the present disclosure.

1—Smart mobile device; 2—Wireless communication module; 3—Sample impedance tester; 4—Embedded control system; 5—Data acquisition module; 6—Signal source module; 7—Bluetooth unit; 8—Wi-Fi hotspot unit; 9—Main control chip; 10—Bluetooth module;

11—Wi-Fi module; 12—Secure digital (SD) card; 13—Parameter setting module; 14—Acquisition control module; 15—Measurement result module; 16—Data visualization module; 17—Data upload module; 18—Software navigation module; 19—Command parsing module; 20—Data receiving and storage module; 21—Data sending module.

DETAILED DESCRIPTION OF THE EMBODIMENTS

To make the to-be-solved technical problems, technical solutions, and advantages of the present disclosure clearer, the present disclosure will be described in detail below with reference to the accompanying drawings and specific embodiments.

In view of the problems that an existing measuring apparatus cannot implement remote measurement, and has low intelligence, poor endurance and slow data transmission speed, the present disclosure provides a system and method for remotely measuring impedance of rock and ore samples.

As shown in FIGS. 1 to 5, an embodiment of the present disclosure provides a system for remotely measuring impedance of rock and ore samples, including: a smart mobile device, where the smart mobile device includes a parameter setting module 13, an acquisition control module 14, a measurement result module 15, a data visualization module 16, a data upload module 17 and a software navigation module 18, where the parameter setting module 13 is configured to set various parameters of sample measurement, the acquisition control module 14 is configured to control an acquisition control process of sample measurement, the measurement result module 15 is configured to perform Fourier transform and calculation on received data and store the data to files of the smart mobile device, the data visualization module 16 is configured to display a measurement result and original data on an interface as a graph, the data upload module 17 is configured to upload various sample-related files in the smart mobile device to a PC end, and the software navigation module 18 is configured to switch between various interfaces and perform function navigation; a wireless communication module, where a first end of the wireless communication module is electrically connected to the smart mobile device, the wireless communication module includes a Bluetooth unit and a Wi-Fi hotspot unit, the Bluetooth unit is configured to send a command, and the Wi-Fi hotspot unit is configured to transmit data; and a sample impedance tester, where the sample impedance tester is electrically connected to a second end of the wireless communication module, the sample impedance tester includes an embedded control system, a data acquisition module and a signal source module, where the embedded control system is configured to receive and send commands and data; a first end of the data acquisition module is electrically connected to the embedded control system, the data acquisition module is configured to receive a control command and acquire data, and a complex programmable logic device (CPLD)-based acquisition system is adopted for the data acquisition module; the signal source module is electrically connected to a second end of the data acquisition module, the data acquisition module is configured to receive a control command and generate an excitation signal, and a signal source board is adopted for the signal source module.

The embedded control system includes: a command parsing module 19, where the command parsing module 19 includes a main control chip, a first end of the main control chip is electrically connected to the first end of the data acquisition module, and the command parsing module 19 is configured to parse a string command from the smart mobile device into a 64-bit hardware command; a data receiving and storage module 20, where the data receiving and storage module 20 includes an SD card, the SD card is electrically connected to a second end of the main control chip, and the data receiving and storage module 20 is configured to receive and store the data acquired by the data acquisition module; and a data sending module 21, where the data sending module 21 includes a Bluetooth module and a Wi-Fi module, where a first end of the Bluetooth module is electrically connected to a third end of the main control chip, a second end of the Bluetooth module is electrically connected to a first end of the Bluetooth unit, and a second end of the Bluetooth unit is electrically connected to an Android phone and a first end of the Wi-Fi hotspot unit; a first end of the Wi-Fi module is electrically connected to a fourth end of the main control chip, a second end of the Wi-Fi module is electrically connected to a second end of the Wi-Fi hotspot unit, a third end of the Wi-Fi hotspot unit is electrically connected to the PC end, and the data sending module 21 is configured to transmit data to the smart mobile device.

In the system and method for remotely measuring impedance of rock and ore samples according to the above embodiments of the present disclosure, the wireless communication module 2 communicates with the embedded control system 4 in two ways: Bluetooth connection and Wi-Fi connection, where the Bluetooth connection is used to send a command, and the Wi-Fi connection is used to transmit data; the parameter setting module 13 is configured to set measurement sample parameters, measurement control parameters, sample information, and the like; the acquisition control module 14 is configured to control a sample measurement process; the measurement result module 15 is configured to store parameter setting information in an SQLite database, store acquired time series as a binary file, perform Fourier transform on the acquired data to obtain a measurement result, and store the measurement result by using a text file; the data visualization module 16 is configured to display, on an interface, the acquired data and the result subjected to data processing as a graph, the software navigation module 18 is configured to switch between various interfaces and perform function navigation, the data upload module 17 uses the Wi-Fi module 11 of the embedded control system 4 as an access point (AP) mode, the PC end and the smart mobile device 1 construct a local area network for station (STA) access, and the smart mobile device 1 uses Wi-Fi connection to send data to the PC end for further processing. The command parsing module 19 is configured to parse a command string sent from the smart mobile device 1, parse plain code into a 64-bit hardware protocol command, and send the command to the acquisition control module 14 for acquisition control; the data sending module 21 is configured to send the data received from the data acquisition module 5 to the smart mobile device 1 by using Wi-Fi connection; and the data receiving and storage module 20 stores acquired original data to the SD card 12. The data acquisition module 5 includes a buffer, a filter circuit and a four-way analog-to-digital converter (ADC). The data acquisition module 5 provides a function of parsing a command from the embedded control system 4 and controlling acquisition. The data acquisition module 5 is configured to uses an ADS1282 high-precision 32-bit ADC for sampling with a CPLD as a control core. The signal source module 6 generates an excitation signal with a certain frequency according to a control command sent by the data acquisition module 5. The signal source module 6 uses a data distribution service (DDS) technology, and is portable and reliable.

In the system and method for remotely measuring impedance of rock and ore samples according to the above embodiments of the present disclosure, the main control chip 9 of the embedded control system 4 is a high-performance 32-bit microcontroller STM32F429IGT6 produced by ST Microelectronics Company, and a kernel of the embedded control system 4 is a Cortex-M4 kernel designed by ARM Company. The main control chip 9 includes 6 serial peripheral interfaces (SPIs), 3 inter-integrated circuits (I2Cs), 1 secure digital input and output (SDIO) interface, 4 universal synchronous/asynchronous receivers/transmitters (USARTs) and 4 universal asynchronous receivers/transmitters (UARTs). SPI1 is configured as a main mode to communicate with the Wi-Fi module 11, can support a transmission speed of 45 Mbps at most, and is configured to transmit the acquired data to the smart mobile device 1. SPI2 and SPI4 communicate with the data acquisition module 5, and SPI4 is a high-speed SPI with a speed as high as 45 Mbps, and is configured to receive data sent from the data acquisition module 5. SPI2 has a maximum speed of 22.5 Mbps and is configured to transmit a control command sent by the embedded control system 4 to the data acquisition module 5. USART1 is connected to the Bluetooth module 10 and interacts with the smart mobile device 1 to acquire a control command sent by the smart mobile device 1.

Figure 3:
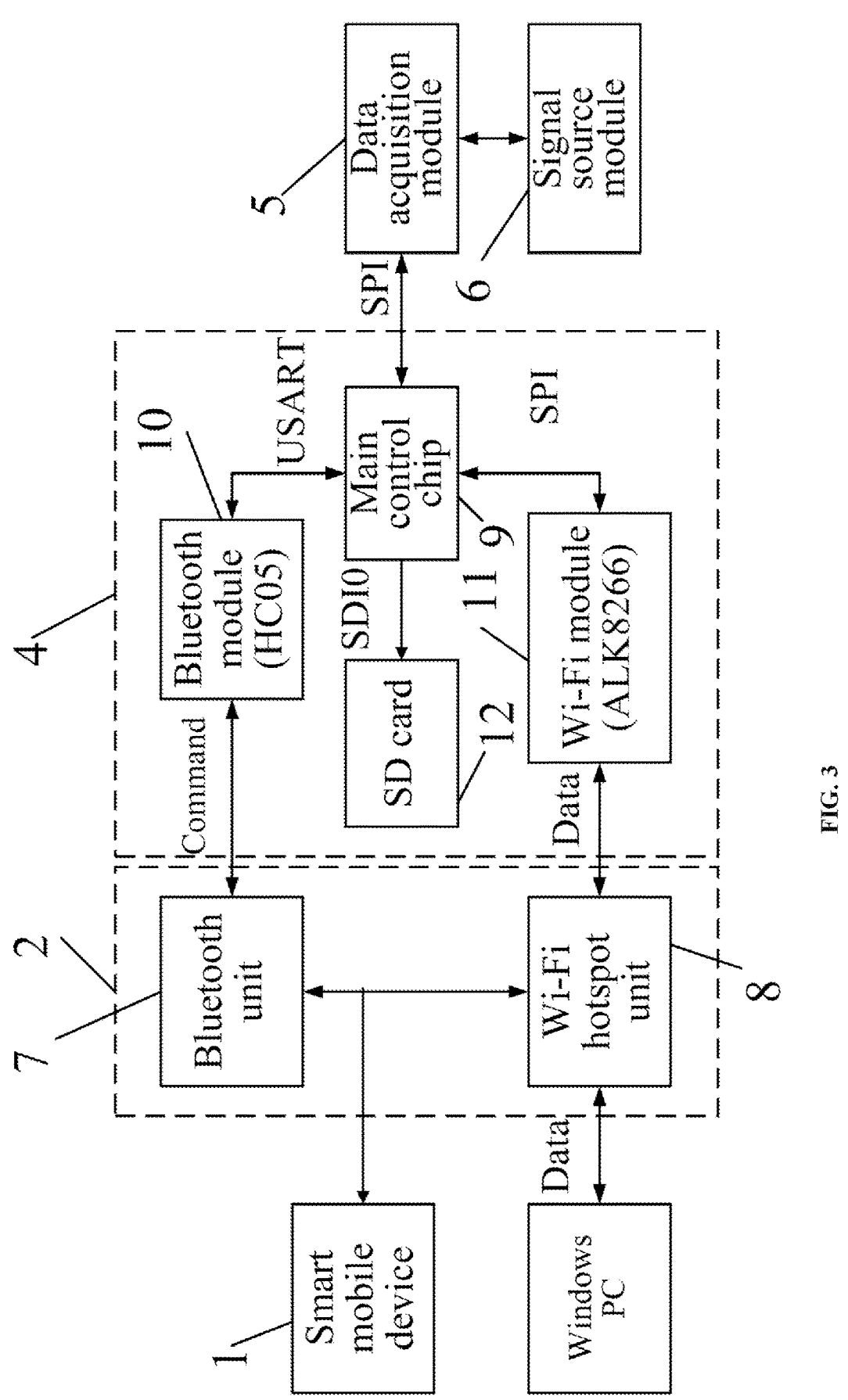
FIG. 3 is a specific schematic structural diagram according to the present disclosure.

As shown in FIG. 3, an embodiment of the present disclosure further provides a method for remotely measuring impedance of rock and ore samples, including the following. Step 1: Establish, by a wireless communication module, wireless network connection between a smart mobile device and a sample impedance tester. Step 2: Perform, by a parameter setting module 13 in the smart mobile device, parameter acquisition setting and sample photographing, and store acquired parameters and photos photographed for the samples. Step 3: Send, by the smart mobile device, a self-check command to the sample impedance tester to obtain self-check information of the sample impedance tester, send, by the smart mobile device, measurement configuration information and an acquisition command to an embedded control system, and parse, by the embedded control system, the received acquisition command. Step 4: Acquire data by a data acquisition module and control a signal source module to generate an excitation signal. Step 5: Store, by the embedded control system, the acquired data and send the data to the smart mobile device. Step 6: Store, by the smart mobile device, the acquired data received and perform Fourier transform, to obtain a data processing result. Step 7: Display, by the smart mobile device, the data processing result as a graph and upload the data processing result to a PC end by means of the wireless communication module.

In the system and method for remotely measuring impedance of rock and ore samples according to the above embodiments of the present disclosure, the method includes the following steps: establishing Wi-Fi and Bluetooth connection between the smart mobile device 1 and the embedded control system 4; setting, on the smart mobile device 1, acquisition parameters and configuring information such as a signal frequency and a sampling rate during self-check, including setting sample parameters, measurement control parameters, sample information and work area information, photographing samples, and storing photos and acquisition parameters; sending a self-check command to the embedded control system 4 to obtain self-check information, calculating after the smart mobile device 1 obtains the data, checking whether the data acquisition module 5, the signal source module 6, and the like can operate normally, and configuring acquisition information after the normal operation is confirmed, to perform formal measurement, where a wireless control mode provides convenience for an operator and achieves higher portability; sending configuration information to the embedded control system 4; sending an acquisition command to the embedded control system 4, where the acquisition command includes plain code such as a signal frequency, a sampling frequency, a measurement signal pattern, a measurement signal amplitude value and a frequency tuning word; performing, by the embedded control system 4, command parsing, where the command parsing means that the embedded control system 4 translates a plain code string into a 64-bit hardware command protocol according to a certain format, and sends the command to the data acquisition module 5 for configuration; receiving, by the data acquisition module 5, the control command and configuring an ADC and the signal source module 6, and acquiring data by the data acquisition module 5 and transmitting the data to the embedded control system 4; receiving, by the signal source module 6, the control command from the data acquisition module 5 to generate an excitation signal; storing and forwarding the data by the embedded control system 4; receiving, by the smart mobile device 1, the data for storage and Fourier transform, storing the data by the smart mobile device 1, receiving, by the smart mobile device 1, a target data volume according to a data volume corresponding to a signal frequency designed by means of a frequency sweep algorithm, and then stopping receiving the data and sending a command for stopping acquiring the data; storing, by the smart mobile device 1, a data processing result and displaying the result as a graph; and uploading, by the smart mobile device 1, the data to the PC end. An Android application (APP) is adopted for the smart mobile device 1. The Android APP features low power consumption, small volume, light weight and convenience in use. Control of the sample impedance tester 3 and data sending are performed by means of Wi-Fi and Bluetooth wireless communication, thereby overcoming the influence of factors such as topography and weather.

Step 1 specifically includes: establishing, by the smart mobile device, wireless connection and communication with the embedded control system in the sample impedance tester by means of a Bluetooth unit and a Wi-Fi hotspot unit of the wireless communication module.

Step 2 specifically includes: setting, by the parameter setting module 13 in the smart mobile device, sample parameters, measurement control parameters, sample information and work area information, photographing the samples, storing, by a measurement result module 15, parameter setting information in an SQLite database, sending, by the parameter setting module 13, set parameter information to an acquisition control module 14, and receiving, by the acquisition control module 14, the parameters from the parameter setting module 13 and controlling a number of measurement times and errors during measurement by means of the received parameters.

In the system and method for remotely measuring impedance of rock and ore samples according to the above embodiments of the present disclosure, the parameter setting module 13 is configured to set sample physical parameters, measurement control information, sample information and geographical position information, store the information in a database, and send the information to the acquisition control module 14 to provide calculation parameters for the acquisition control module 14. After receiving the parameters from the parameter setting module 13, the acquisition control module 14 uses these parameters to control a time of measurement times, errors, and the like in the measurement process during acquisition.

Step 3 specifically includes: sending, by the smart mobile device, the self-check command to the sample impedance tester, receiving, by the sample impedance tester, the self-check command sent by the smart mobile device to obtain self-check information, sending, by the smart mobile device, measurement configuration information and an acquisition command to the embedded control system, the acquisition command including a signal frequency, a sampling frequency, a measurement signal pattern, a measurement signal amplitude value and a frequency tuning word, parsing, by the embedded control system, the acquisition command by means of a command parsing module 19, and parsing a plain code string into a 64-bit hardware protocol command and sending the command to the data acquisition module for acquisition control.

In the system and method for remotely measuring impedance of rock and ore samples according to the above embodiments of the present disclosure, the command parsing module 19 is configured to receive, in the embedded control system 4 and by Bluetooth connection, plain code, that is, a string command, sent by the smart mobile device 1, translate the string command into a 64-bit hardware protocol agreed with the data acquisition module 5 by means of a parsing function, and allow the data acquisition module 5 to configure its own parameters and parameters of the signal source module 6.

Step 4 specifically includes: receiving, by the data acquisition module, a control command from the embedded control system to configure an ADC and the signal source module, acquiring the data by the data acquisition module and transmitting the acquired data to the embedded control system, and receiving, by the signal source module, the control command from the data acquisition module and generating the excitation signal.

In the system and method for remotely measuring impedance of rock and ore samples according to the above embodiments of the present disclosure, the data acquisition module 5 is configured to control the acquisition of the ADC with the CPLD as a control core and control the generation of signal source excitation. After receiving the configuration command sent by the data acquisition module 5, the signal source module 6 configures and generates a current or voltage source required by a user and a specified value.

Step 5 specifically includes: receiving, by a data receiving and storage module 20, the acquired data from the data acquisition module, storing, by the data receiving and storage module 20, the acquired data to an SD card of the embedded control system, and transmitting, by the data sending module 21, the acquired data to the smart mobile device.

In the system and method for remotely measuring impedance of rock and ore samples according to the above embodiments of the present disclosure, after the signal source generates excitation, the data acquisition module 5 starts to acquire data, and the data acquired by the data acquisition module 5 is continuously sent to the embedded control system 4 by means of an SPI. The data receiving and storage module 20 stores the data in the SD card 12 of the embedded control system 4, and the data sending module 21 sends, by using the Wi-Fi module 11 of the embedded control system 4, the data acquired from the data acquisition module 5 to the smart mobile device 1 in time for processing.

Step 6 specifically includes: storing, by the smart mobile device, the acquired data received, receiving, by the smart mobile device, a target data volume according to a data volume corresponding to a signal frequency designed by means of a frequency sweep algorithm, and then stopping receiving the acquired data and sending a command for stopping acquiring the data; performing, by the measurement result module 15, Fourier transform on the acquired data received from the data acquisition module, calculating the acquired data, obtaining a response generated by the rock and ore samples under excitation of the signal frequency, and storing original data and a measurement result, where the original data is time domain binary data and is directly stored in a file, and the measurement result is written into a text file in a fixed format.

In the system and method for remotely measuring impedance of rock and ore samples according to the above embodiments of the present disclosure, the measurement result module 15 is configured to perform Fourier transform on the acquired data received from the data acquisition module 5, calculate each piece of data, obtain a response generated by the rock and ore samples under excitation of the signal frequency, and store original data and a measurement result, where the original data is time domain binary data and is directly stored in a file, and the measurement result is written into a text file in a fixed format.

Step 7 specifically includes: reading, by a data visualization module 16, all previous measurement results and displaying all the previous measurement results on an interface as a graph by using an Android drawing framework, processing, by a data upload module 17, a sample photo, a time series file and a result file corresponding to each measured sample in a work area and a database file corresponding to the work area, building a local area network by using the smart mobile device, and uploading the entire work area file to the PC end by means of transmission control protocol (TCP) transmission.

In the system and method for remotely measuring impedance of rock and ore samples according to the above embodiments of the present disclosure, after the measurement result module 15 stores a current measurement result in a text file according to a fixed format, the data visualization module 16 is configured to read all previous measurement results and display the data as a graph on an interface by using an Android drawing framework, where the generated graph includes: a time domain original data graph and a phase and resistivity spectrum map. After the data upload module 17 completes the measurement of all samples in a work area, the data upload module 17 is configured to further process a sample photo, a time series file and a result file corresponding to each sample and a database file corresponding to the work area, and the data upload module 17 is configured to build a simple local area network by using the smart mobile device 1, and upload the entire work area file to the PC end by means of TCP transmission. In order to improve the uploading speed, the data upload module 17 uses a Zip compression algorithm to compress an entire work area folder, which greatly improves the transmission efficiency.

Figure 4:
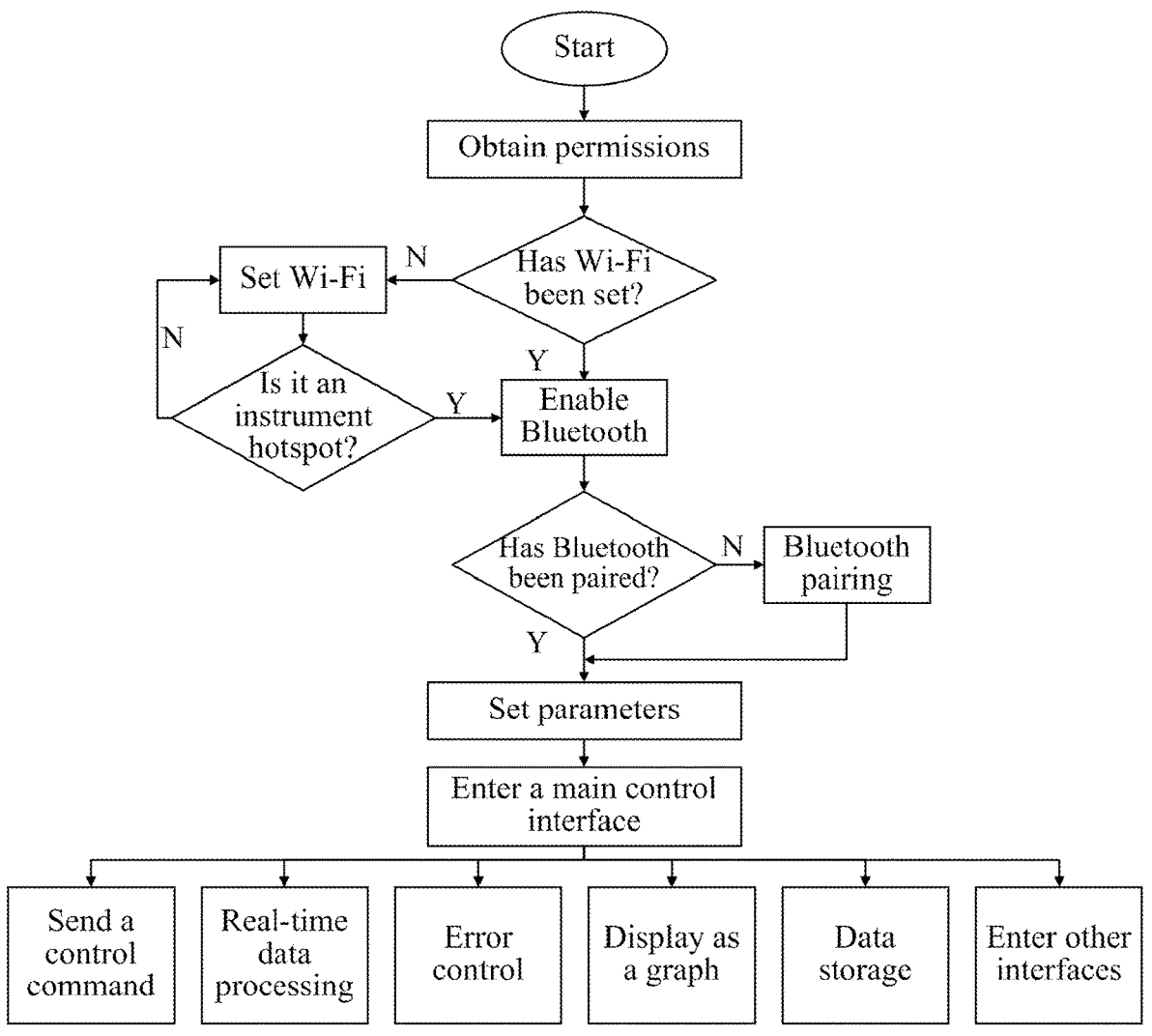
FIG. 4 is an operation flowchart of a smart mobile device according to the present disclosure.

In the system and method for remotely measuring impedance of rock and ore samples according to the above embodiments of the present disclosure, as shown in FIG. 4, when the smart mobile device 1 is started, permissions to normally use software for location, file reading and writing, and the like are first obtained, then a Wi-Fi setting interface is entered, the user connects a hotspot, and the smart mobile device 1 automatically determines whether the currently connected hotspot is an instrument hotspot, and prompts the user to set; during communication with the embedded control system 4, the smart mobile device 1 initiates TCP connection as a client to establish a data transmission channel with the embedded control system 4, and then Bluetooth is enabled for pairing and connection with the Bluetooth module 10 of the embedded control system 4 to establish a command transmission channel; the parameters are inputted by the parameter setting module 13 for saving and transmitted to an acquisition control interface, data acquisition is performed after self-check and calibration, and data processing, error control and measurement result storage are performed during the acquisition.

Figure 5:
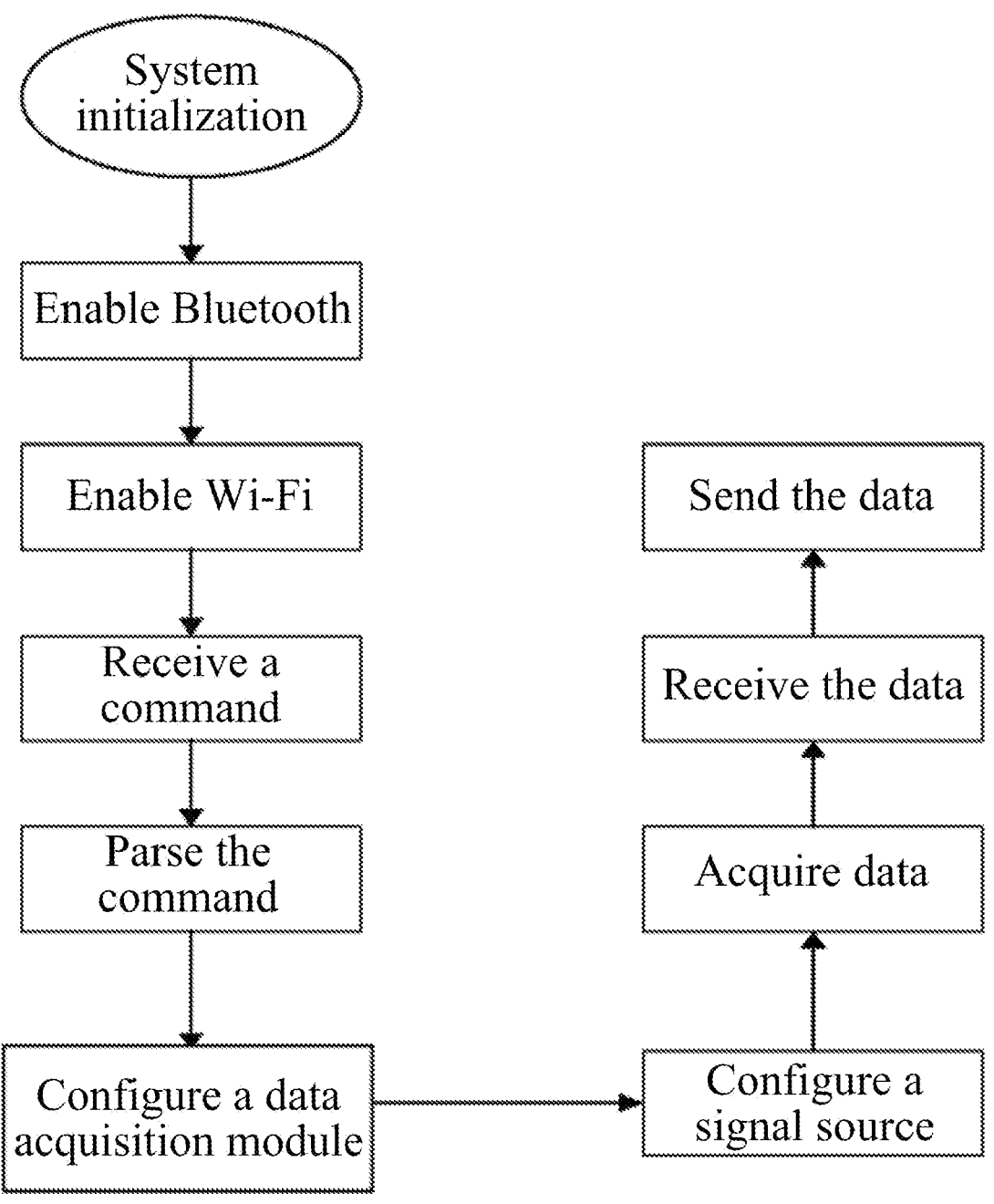
FIG. 5 is an operation flowchart of a sample impedance tester according to the present disclosure.

In the system and method for remotely measuring impedance of rock and ore samples according to the above embodiments of the present disclosure, as shown in FIG. 5, the sample impedance tester 3 performs system initialization, automatically enables Bluetooth and Wi-Fi after the system initialization to establish wireless connection, receives a string command sent by the smart mobile device 1 and then parses the command to obtain a 64-bit hardware command protocol, and then configures the data acquisition module 5 and the signal source module 6; the signal source module 6 generates an excitation signal, and rock and ore samples respond; the data acquisition module 5 sends the acquired data to the embed control system 4, and the embedded control system 4 uploads the acquired data to the smart mobile device 1, with a high data transmission speed.

In the system and method for remotely measuring impedance of rock and ore samples according to the above embodiments of the present disclosure, through wireless interaction between the smart mobile device 1 and the sample impedance tester 3, remote measurement is implemented, and the sample impedance tester 3 can send the measured data to the smart mobile device 1 in real time, so that the smart mobile device 1 can continuously monitor the sample impedance tester 3, and can calculate data to obtain the sample impedance of rocks and ores at a frequency point.

The foregoing are descriptions of preferred implementations of the present disclosure. It should be noted that those of ordinary skill in the art can make several improvements and modifications without departing from the principle of the present disclosure, and such improvements and modifications should be deemed as falling within the protection scope of the present disclosure.

What is claimed is:

1. A system for remotely measuring impedance of rock and ore samples, comprising:
   a smart mobile device, wherein the smart mobile device comprises a parameter setting module, an acquisition control module, a measurement result module, a data visualization module, a data upload module and a software navigation module, wherein the parameter setting module is configured to set various parameters of sample measurement, the acquisition control module is configured to control an acquisition control process of sample measurement, the measurement result module is configured to perform Fourier transform and calculation on received data and store the data to files of the smart mobile device, the data visualization module is configured to display a measurement result and original data on an interface as a graph, the data upload module is configured to upload various sample-related files in the smart mobile device to a personal computer (PC) end, and the software navigation module is configured to switch between various interfaces and perform function navigation;

a wireless communication module, wherein a first end of the wireless communication module is electrically connected to the smart mobile device, the wireless communication module comprises a Bluetooth unit and a wireless fidelity (Wi-Fi) hotspot unit, the Bluetooth unit is configured to send a command, and the Wi-Fi hotspot unit is configured to transmit data; and a sample impedance tester, wherein the sample impedance tester is electrically connected to a second end of the wireless communication module, the sample impedance tester comprises an embedded control system, a data acquisition module and a signal source module, wherein the embedded control system is configured to receive and send commands and data; a first end of the data acquisition module is electrically connected to the embedded control system, the data acquisition module is configured to receive a control command and acquire data, and a complex programmable logic device (CPLD)-based acquisition system is adopted for the data acquisition module; the signal source module is electrically connected to a second end of the data acquisition module, the data acquisition module is configured to receive a control command and generate an excitation signal, and a signal source board is adopted for the signal source module.

2. The system for remotely measuring impedance of rock and ore samples according to claim 1, wherein the embedded control system comprises:

a command parsing module, wherein the command parsing module comprises a main control chip, a first end of the main control chip is electrically connected to the first end of the data acquisition module, and the command parsing module is configured to parse a string command from the smart mobile device into a 64-bit hardware command;

a data receiving and storage module, wherein the data receiving and storage module comprises a secure digital (SD) card, the SD card is electrically connected to a second end of the main control chip, and the data receiving and storage module is configured to receive and store the data acquired by the data acquisition module; and a data sending module, wherein the data sending module comprises a Bluetooth module and a Wi-Fi module, wherein a first end of the Bluetooth module is electrically connected to a third end of the main control chip, a second end of the Bluetooth module is electrically connected to a first end of the Bluetooth unit, and a second end of the Bluetooth unit is electrically connected to an Android phone and a first end of the Wi-Fi hotspot unit; a first end of the Wi-Fi module is electrically connected to a fourth end of the main control chip, a second end of the Wi-Fi module is electrically connected to a second end of the Wi-Fi hotspot unit, a third end of the Wi-Fi hotspot unit is electrically connected to the PC end, and the data sending module is configured to transmit data to the smart mobile device.

3. A method for remotely measuring impedance of rock and ore samples, which is applied to the system for remotely measuring impedance of rock and ore samples according to claim 2, comprising:

step 1: establishing, by a wireless communication module, wireless network connection between a smart mobile device and a sample impedance tester;

step 2: performing, by a parameter setting module in the smart mobile device, parameter acquisition setting and sample photographing, and storing acquired parameters and photos photographed for the samples;

step 3: sending, by the smart mobile device, a self-check command to the sample impedance tester to obtain self-check information of the sample impedance tester, sending, by the smart mobile device, measurement configuration information and an acquisition command to an embedded control system, and parsing, by the embedded control system, the received acquisition command;

step 4: acquiring data by a data acquisition module and controlling a signal source module to generate an excitation signal;

step 5: storing, by the embedded control system, the acquired data and sending the data to the smart mobile device;

step 6: storing, by the smart mobile device, the acquired data received and performing Fourier transform, to obtain a data processing result; and step 7: displaying, by the smart mobile device, the data processing result as a graph and uploading the data processing result to a PC end by means of the wireless communication module.

4. The method for remotely measuring impedance of rock and ore samples according to claim 3, wherein step 1 specifically comprises:

establishing, by the smart mobile device, wireless connection and communication with the embedded control system in the sample impedance tester by means of a Bluetooth unit and a Wi-Fi hotspot unit of the wireless communication module.

5. The method for remotely measuring impedance of rock and ore samples according to claim 4, wherein step 2 specifically comprises:

setting, by the parameter setting module in the smart mobile device, sample parameters, measurement control parameters, sample information and work area information, photographing the samples, storing, by a measurement result module, parameter setting information in an SQLite database, sending, by the parameter setting module, set parameter information to an acquisition control module, and receiving, by the acquisition control module, the parameters from the parameter setting module and controlling a number of measurement times and errors during measurement by means of the received parameters.

6. The method for remotely measuring impedance of rock and ore samples according to claim 5, wherein step 3 specifically comprises:

sending, by the smart mobile device, the self-check command to the sample impedance tester, receiving, by the sample impedance tester, the self-check command sent by the smart mobile device to obtain self-check information, sending, by the smart mobile device, measurement configuration information and an acquisition command to the embedded control system, the acquisition command comprising a signal frequency, a sampling frequency, a measurement signal pattern, a measurement signal amplitude value and a frequency tuning word, parsing, by the embedded control system, the acquisition command by means of a command parsing module, and parsing a plain code string into a 64-bit hardware protocol command and sending the command to the data acquisition module for acquisition control.

7. The method for remotely measuring impedance of rock and ore samples according to claim 6, wherein step 4 specifically comprises:

receiving, by the data acquisition module, a control command from the embedded control system to configure an analog-to-digital converter (ADC) and the signal source module, acquiring the data by the data acquisition module and transmitting the acquired data to the embedded control system, and receiving, by the signal source module, the control command from the data acquisition module and generating the excitation signal.

8. The method for remotely measuring impedance of rock and ore samples according to claim 7, wherein step 5 specifically comprises:

receiving, by a data receiving and storage module, the acquired data from the data acquisition module, storing, by the data receiving and storage module, the acquired data to an SD card of the embedded control system, and transmitting, by the data sending module, the acquired data to the smart mobile device.

9. The method for remotely measuring impedance of rock and ore samples according to claim 8, wherein step 6 specifically comprises:

storing, by the smart mobile device, the acquired data received, receiving, by the smart mobile device, a target data volume according to a data volume corresponding to a signal frequency designed by means of a frequency sweep algorithm, and then stopping receiving the acquired data and sending a command for stopping acquiring the data; performing, by the measurement result module, Fourier transform on the acquired data received from the data acquisition module, calculating the acquired data, obtaining a response generated by the rock and ore samples under excitation of the signal frequency, and storing original data and a measurement result, wherein the original data is time domain binary data and is directly stored in a file, and the measurement result is written into a text file in a fixed format.

10. The method for remotely measuring impedance of rock and ore samples according to claim 9, wherein step 7 specifically comprises:

reading, by a data visualization module, all previous measurement results and displaying all the previous measurement results on an interface as a graph by using an Android drawing framework, processing, by a data upload module, a sample photo, a time series file and a result file corresponding to each measured sample in a work area and a database file corresponding to the work area, building a local area network by using the smart mobile device, and uploading the entire work area file to the PC end by means of transmission control protocol (TCP) transmission.

11. A method for remotely measuring impedance of rock and ore samples, which is applied to the system for remotely measuring impedance of rock and ore samples according to claim 1, comprising:

step 1: establishing, by a wireless communication module, wireless network connection between a smart mobile device and a sample impedance tester;

step 2: performing, by a parameter setting module in the smart mobile device, parameter acquisition setting and sample photographing, and storing acquired parameters and photos photographed for the samples;

step 3: sending, by the smart mobile device, a self-check command to the sample impedance tester to obtain self-check information of the sample impedance tester, sending, by the smart mobile device, measurement configuration information and an acquisition command to an embedded control system, and parsing, by the embedded control system, the received acquisition command;

step 4: acquiring data by a data acquisition module and controlling a signal source module to generate an excitation signal;

step 5: storing, by the embedded control system, the acquired data and sending the data to the smart mobile device;

step 6: storing, by the smart mobile device, the acquired data received and performing Fourier transform, to obtain a data processing result; and step 7: displaying, by the smart mobile device, the data processing result as a graph and uploading the data processing result to a PC end by means of the wireless communication module.

12. The method for remotely measuring impedance of rock and ore samples according to claim 11, wherein step 1 specifically comprises:

establishing, by the smart mobile device, wireless connection and communication with the embedded control system in the sample impedance tester by means of a Bluetooth unit and a Wi-Fi hotspot unit of the wireless communication module.

13. The method for remotely measuring impedance of rock and ore samples according to claim 12, wherein step 2 specifically comprises:

setting, by the parameter setting module in the smart mobile device, sample parameters, measurement control parameters, sample information and work area information, photographing the samples, storing, by a measurement result module, parameter setting information in an SQLite database, sending, by the parameter setting module, set parameter information to an acquisition control module, and receiving, by the acquisition control module, the parameters from the parameter setting module and controlling a number of measurement times and errors during measurement by means of the received parameters.

14. The method for remotely measuring impedance of rock and ore samples according to claim 13, wherein step 3 specifically comprises:

sending, by the smart mobile device, the self-check command to the sample impedance tester, receiving, by the sample impedance tester, the self-check command sent by the smart mobile device to obtain self-check information, sending, by the smart mobile device, measurement configuration information and an acquisition command to the embedded control system, the acquisition command comprising a signal frequency, a sampling frequency, a measurement signal pattern, a measurement signal amplitude value and a frequency tuning word, parsing, by the embedded control system, the acquisition command by means of a command parsing module, and parsing a plain code string into a 64-bit hardware protocol command and sending the command to the data acquisition module for acquisition control.

15. The method for remotely measuring impedance of rock and ore samples according to claim 14, wherein step 4 specifically comprises:

receiving, by the data acquisition module, a control command from the embedded control system to configure an analog-to-digital converter (ADC) and the signal source module, acquiring the data by the data acquisition module and transmitting the acquired data to the embedded control system, and receiving, by the signal source module, the control command from the data acquisition module and generating the excitation signal.

16. The method for remotely measuring impedance of rock and ore samples according to claim 15, wherein step 5 specifically comprises:

receiving, by a data receiving and storage module, the acquired data from the data acquisition module, storing, by the data receiving and storage module, the acquired data to an SD card of the embedded control system, and transmitting, by the data sending module, the acquired data to the smart mobile device.

17. The method for remotely measuring impedance of rock and ore samples according to claim 16, wherein step 6 specifically comprises:

storing, by the smart mobile device, the acquired data received, receiving, by the smart mobile device, a target data volume according to a data volume corresponding to a signal frequency designed by means of a frequency sweep algorithm, and then stopping receiving the acquired data and sending a command for stopping acquiring the data; performing, by the measurement result module, Fourier transform on the acquired data received from the data acquisition module, calculating the acquired data, obtaining a response generated by the rock and ore samples under excitation of the signal frequency, and storing original data and a measurement result, wherein the original data is time domain binary data and is directly stored in a file, and the measurement result is written into a text file in a fixed format.

18. The method for remotely measuring impedance of rock and ore samples according to claim 17, wherein step 7 specifically comprises:

reading, by a data visualization module, all previous measurement results and displaying all the previous measurement results on an interface as a graph by using an Android drawing framework, processing, by a data upload module, a sample photo, a time series file and a result file corresponding to each measured sample in a work area and a database file corresponding to the work area, building a local area network by using the smart mobile device, and uploading the entire work area file to the PC end by means of transmission control protocol (TCP) transmission.

* * * * *